United States Patent [19]
Richard et al.

[11] Patent Number: 5,928,500
[45] Date of Patent: Jul. 27, 1999

[54] REMOVAL OF HALOGENATED ORGANIC COMPOUNDS FROM HYDROCARBON STREAMS

[75] Inventors: Michael A. Richard, Houston, Tex.; Vyacheslav Gurevich, San Mateo; Carlos E. Faz, Hayward, both of Calif.

[73] Assignee: Catalytica Incorporated, Mountain View, Calif.

[21] Appl. No.: 08/947,099

[22] Filed: Oct. 8, 1997

[51] Int. Cl.[6] .......................... C10G 25/00; C10G 25/12; C07C 7/12
[52] U.S. Cl. ...................... 208/262.1; 208/262.5; 208/299; 208/305; 585/820; 823/826
[58] Field of Search .................... 308/262.1, 262.5, 308/299, 305; 585/820, 823, 826; 502/50, 53

[56] References Cited

U.S. PATENT DOCUMENTS

| | | | |
|---|---|---|---|
| 2,164,334 | 7/1939 | Marks | 208/262.1 |
| 2,328,707 | 9/1943 | Clar et al. | 208/262.1 |
| 2,347,945 | 5/1944 | Frey | 208/262.1 |
| 2,409,372 | 10/1946 | Matuszak | 208/262.1 |
| 3,862,900 | 1/1975 | Reusser | 208/262.1 |
| 3,864,243 | 2/1975 | Reusser et al. | 208/262.1 |
| 3,925,193 | 12/1975 | Constantikes et al. | 208/262.1 |
| 3,935,295 | 1/1976 | La Hue et al. | 208/262.1 |
| 4,382,879 | 5/1983 | Funabashi et al. | 502/407 |
| 4,721,824 | 1/1988 | McWilliams et al. | 208/262.1 |
| 5,130,282 | 7/1992 | Bodart et al. | 502/34 |

*Primary Examiner*—Walter D. Griffin
*Attorney, Agent, or Firm*—Al A. Jecminek

[57] ABSTRACT

This invention is a process for removing minor amounts of organic halide e.g., organic chloride, contaminants from hydrocarbon feedstocks by contact with a regenerable solid adsorbent comprising a metal and/or metal hydride selected from nickel, cobalt or iron, or mixtures thereof on a porous refractory support, such as silica, whereby the halide present in the hydrocarbon feedstock is converted substantially to an insoluble metal halide salt of the supported metal or metal hydride with the hydrocarbon feedstock being recovered from the contacting step substantially free of organic halide contaminant. Also disclosed is a process for regeneration of the adsorbent loaded with metal halide from the hydrocarbon feedstock contacting step and an integrated process where the regenerated adsorbent is reused to remove additional organic halide from the hydrocarbon feedstock.

13 Claims, No Drawings

REMOVAL OF HALOGENATED ORGANIC COMPOUNDS FROM HYDROCARBON STREAMS

FIELD OF THE INVENTION

This invention relates to a process for removing small or trace amounts of halogenated organic impurities from hydrocarbon streams containing aliphatic, olefinic, aromatic and/or oxygenated components by means of contact with a solid adsorbent comprising a regenerable metal and/or metal hydride deposited on a refractory support. More particularly, this invention is directed to an improved process for removing halogenated organic compounds, particularly organic chlorides, present in minor amounts in the aforesaid hydrocarbon stream by contact with a metal or metal hydride selected from nickel, cobalt and/or iron on a porous refractory support, such as silica or alumina, whereby substantially complete removal of the halogen component can be obtained with minimal effect on the other organic components contained in the hydrocarbon stream. Also, within this invention is a method by which the halogen-loaded, metal adsorbent can be regenerated for reuse in the organic halide removal process.

BACKGROUND OF THE INVENTION

In a variety of chemical, petrochemical and refinery processes, organic process streams, for example, light and heavy naphtha, raffinate, oxygenates etc., or waste streams are generated which contain minor or trace amounts of halogenated organic compounds as undesired by products or contaminants. These halogenated organic impurities can interfere with the recycle, disposal and/or subsequent use of the contaminated process or waste stream, for example, by poisoning catalysts or corroding process equipment, in the case of recycle or further use of the contaminated process stream, or by upsetting biotreatment or other waste treatment processes, in the case of waste stream treatment or disposal.

Past efforts to remove halogenated organic contaminants from hydrocarbon process or waste streams have focused on the use of catalytic hydrogenation, generally in the presence of a noble metal catalyst, to convert the organic halide to a hydrogen halide which is typically removed and/or recovered by caustic treatment. However, when hydrocarbon streams containing reducible components, i.e., unsaturated and/or oxygenated compounds, are employed, the conditions of the catalytic hydrogenation reaction, which involve the presence of molecular hydrogen or a hydrogen donor and elevated reaction temperatures, typically result in significant conversion of the reducible components to their hydrogenated or reduced form. Further, the use of catalytic hydrogenation to remove organic halide contaminants requires a more complicated and expensive process in terms of reactants, equipment and process controls than would otherwise be desired. This is because the catalytic hydrogenation reaction requires large quantities of expensive hydrogen reactant and must be closely controlled in terms of reactant ratios, temperatures, times and pressures. Further, the product separation, particularly where gaseous hydrogen halide must be separated from volatile hydrocarbons, can be difficult to accomplish. Finally, in many cases the hydrogenation catalysts are not readily regenerable and therefore must be replaced periodically as their activity falls off.

For example, U.S. Pat. Nos. 3,892,818; 4,8181,368; 4,840,721, 4,902,842; 4,923,590; 5,314,614; 5,316,663 and 5,401,894 all disclose processes wherein an organic halide is removed via reaction with hydrogen in the presence of a hydrogenation catalyst. U.S. Pat. No. 4,925,998 discloses a variation of this general process for dehydrohalogenation of aromatic halides where the reaction with hydrogen is carried out in the presence of a Group VIII metal catalyst and a compound capable of forming alkyl halide under the reaction conditions selected. An alternative technique is disclosed in U.S. Pat. No. 4,618,686 where it is taught that aromatic and alpha-araliphatic halides can be dehalogenated by reaction with a hypophosphite salt in the presence of a hydrogenation catalyst. Other references showing catalytic hydrogenation as a means of dechlorinating organic feedstreams include Ger. Offen. No. 2,127,182 and Japanese Kokai No. 81,133,221.

Other documented efforts in the prior art to remove organic halide contaminants from various hydrocarbon feedstreams include that disclosed in U.S. Patent No. 3,935,295 where an admixture of zinc oxide and a basic compound of calcium with an inert binder is used to remove HCl formed on hydrotreatment of a liquid hydrocarbon feedstock and in U.S. Pat. No. 4,417,091 where a solid absorbent such as silica, alumina, silica-alumina or an activated earth is used to remove fluorine and/or fluorinated compounds from the olefin product produced by oligomerization of monoolefins over a nickel/aluminum halide catalyst containing a Bronstead acid such as trifluoroacetic acid. In at least the first case (U.S. Pat. No. 3,935,295), the adsorption step must be preceded by catalytic hydrogenation to convert any organic chloride present to HCl.

Accordingly it is apparent that a continuing need exists for new methods of removing organic halide contaminants from hydrocarbon feedstreams which avoid the problems associated with the prior art catalytic hydrogenation processes in terms of cost and complexity and which minimize the loss of reducible components present in the hydrocarbon feed. The present invention provides such a process where losses of reducible components are minimized in a simple and cost-effective way using a regenerable solid adsorbent for organic halide contaminants contained in the hydrocarbon feedstream.

SUMMARY OF THE INVENTION

It has now been found that certain metals and/or metal hydrides loaded on high surface area, porous, refractory supports are highly effective in selectively removing minor amounts of organic halides (and, to the extent present, certain inorganic halides) from hydrocarbon feedstreams which may also contain a variety of reactive or reducible organic components. This finding is based on the discovery that the halides present in the hydrocarbon feedstream react selectively with the supported metal and/or metal hydride to form an insoluble metal halide under conditions which are sufficiently mild that losses of reactive or reducible components, e.g., unsaturated or oxygenated hydrocarbons, are reduced or held at very low levels relative to prior art hydrogenation processes. Further, it has also been found that these supported metal and/or metal hydride adsorbents are readily regenerable (after being loaded with halide in the form of metal halide) by sequential treatment with a reducing atmosphere, for example hydrogen, followed by an oxidizing gas such as air or oxygen and finally for a second time with the reducing or molecular hydrogen-containing atmosphere. The product of the regeneration process is readily reusable in the organic halide removal process of this invention.

Accordingly, in its broadest terms, the invention is an improved process for removing organic halides present in minor amounts in a hydrocarbon feedstock which comprises contacting the hydrocarbon feedstock with a solid adsorbent comprising a metal and metal hydride or mixture of metal and metal hydride wherein the metal is selected from nickel, cobalt and iron or mixtures thereof, on a porous, high surface area, refractory support whereby at least a substantial portion of the organic halide present is converted to an insoluble halide salt of the supported metal or metal hydride, and thereby removed from the hydrocarbon feedstock, with the hydrocarbon feedstock being recovered after contact with the solid absorbent substantially free of inorganic or organic halide contaminants.

Another aspect of the invention is directed to a process for regenerating the solid adsorbent, loaded with metal halide from the hydrocarbon feedstock contacting step, set forth above, which comprises an optional first step of contacting the metal halide loaded adsorbent with a reducing atmosphere, such as molecular hydrogen, at elevated temperatures to convert the metal halide to its metallic or reduced form followed by a) treating the solid adsorbent product of the optional first step with an oxidizing or oxygen-containing medium at elevated temperatures to remove any carbonaceous or organic deposits on the surface of the solid adsorbent and to convert the reduced metal to its oxide form; and b) treating the solid adsorbent product of step a) with a reducing or hydrogen-containing atmosphere to convert the metal oxide to its metallic or metal hydride form.

In a final and preferred aspect of the invention the regeneration process described above is combined with the halide removal process to provide an integrated process for removing minor amounts of organic halides from hydrocarbon feedstreams containing said halide components which comprises:

a) Contacting the hydrocarbon feedstream with a solid adsorbent comprising a metal or metal hydride or mixture thereof wherein the metal is selected from nickel, cobalt and iron or mixtures thereof on a porous, high surface area, refractory support whereby substantially all of the halide present in the hydrocarbon feedstream reacts with the metal or metal hydride to form an insoluble metal halide thereby affording a hydrocarbon feedstream product substantially free of halide and a solid adsorbent loaded with metal halide.

b) Separating the metal halide loaded adsorbent from the hydrocarbon feedstream, substantially free of halide and contacting the separated adsorbent in sequential fashion with (i) a reducing atmosphere to convert the metal halide to its metallic or reduced form, (ii) an oxidizing medium to remove any carbonaceous or organic deposits on the surface of the adsorbent thereby converting the metallic or reduced form of the metal to its oxide form, and (iii) a reducing atmosphere to convert the metal oxide to its reduced or metallic form thereby affording a regenerated solid adsorbent.

c) Recycling the regenerated solid adsorbent back to step a) of the process where it is used to remove additional halide from the hydrocarbon feedstream.

DESCRIPTION OF THE INVENTION

The hydrocarbon feedstreams, contaminated with organic halides, which are usefully treated in the process of the inventions to remove the organic halide contaminants, include a wide variety of hydrocarbon-containing product and by-product streams from refineries, petrochemical and chemical plants, for example light and heavy naphtha, raffinate, oxygenates or other functionalized but nonhalogenated hydrocarbons, by-product streams from refrigerant manufacture or disposal and the like. In addition to the organic halide contaminants, the hydrocarbon feedstock may suitably be comprised of one or more hydrocarbon components including both saturated and unsaturated aliphatic components; aromatic and heterocyclic components, (including alkaryl compounds); oxygenated compounds such as alcohols, ketones, aldehydes, ethers and esters or mixtures thereof; other functionalized hydrocarbons containing for example substituents such as thiol, sufinyl, sulfonyl, phosphinyl, phosphonyl, silanoyl and the like which are non-reactive with the metal or metal hydride on the solid adsorbent under the hydrocarbon feedstock contacting conditions. Preferred hydrocarbon feedstocks include hydrocarbon streams, containing paraffinic hydrocarbons, e.g., alkanes or cycloalkanes, of up to 20 carbon atoms; olefinic hydrocarbons including alkenes, dienes and polyunsaturated olefins of up to 20 carbon atoms as well as oligomers thereof; oxygenated hydrocarbons containing up to 20 carbon atoms and at least one oxygen containing group selected from hydroxy, oxy, —C(O)R, —COR'R and —C—OR where R and R' may be the same or different and each represents an alkyl and alkenyl, alkaryl or aralkyl group; and aromatic compounds of up to 20 carbon atoms including bicyclic, and polycyclic aromatic compounds.

While it is preferred that the hydrocarbon feedstock be liquid or gaseous in form at ambient temperatures, more viscous or solid hydrocarbons can be diluted or dissolved in liquid hydrocarbon solvents prior to treatment in the process of the invention to remove organic halide contaminants. Suitable hydrocarbon solvents in this regard include $C_5$ to $C_8$ straight or branched chain alkanes, and cycloalkanes; aromatic solvents including benzene, toluene and xylene; and oxygenated solvents such as acetone, methyl ethyl ketone, isopropylalcohol, cyclohexanol, methyl ethyl ether, ethyl acetate, and the like.

The organic halide contaminant or contaminants present in the hydrocarbon feedstream which is treatable in the process of the invention include halogenated hydrocarbons of up to about 30 carbon atoms substituted with one or more halogens selected from fluorine, bromine, chlorine and iodine. Preferably, the organic halide contaminant is a chloride or bromide with chlorides being most preferred. The extent of halogen substitution on the organic halide can vary between broad limits, with halide contents of between about 1 to 80% by weights being suitable. While other non-reactive functional groups may be present on the organic halide contaminant, it is preferred that the hydrocarbon contaminant contain only the halide as the heteroatom. Typically the organic halide contaminant is a straight or branched chain or cycloaliphatic hydrocarbon which may be saturated or unsaturated of up to 20 carbon atoms, optionally substituted with saturated or unsaturated aliphatic radicals, or an aromatic hydrocarbon of up to 14 carbon atoms, substituted with saturated or unsaturated aliphatic radicals, with one or more, preferably 1 to 6 of the hydrogen atoms on the aliphatic radicals being replaced with halogen, preferably chlorine. The process appears to be less effective with aromatic halides where the halogen atoms are present only as ring substituents, therefore, it is preferred that the amount of aromatic halide with ring halide substituents in the hydrocarbon feedstock be minimized. Most preferably, the organic halide contaminant is a straight chain or branched chain or cycloalkane of up to 9 carbon atoms containing 1 to 6 chlorine atoms. In any given case, the organic halide contaminant may be present as single component or more likely may comprise a mixture of halogenated components having compositions given above.

Hydrocarbon feedstocks which are treatable in the process of the invention typically contain minor amounts, that is, less than about 5 per cent by weight organic halide contaminant. Preferably, the organic halide contaminant is an organic chloride present in the 10 to 10,000 ppm range based on total hydrocarbon feedstock weight, with feedstocks containing between about 500 to about 5000 ppm of organic chloride contaminant being most preferred.

The metal and/or metal hydride solid adsorbent employed in the process of the invention suitably comprises a metal or metal hydride selected from nickel, cobalt and iron or mixtures thereof, with nickel being preferred. In general the metal and/or metal hydride may comprise from about 5 to 75 percent by weight of the solid adsorbent, with nickel contents of from about 10 to 60 percent by weight being most suitable for the preferred nickel and/or nickel hydride adsorbents. Most preferably, the nickel content of the preferred adsorbents is between about 30 and 60 percent by weight of the solid absorbent. The porous, high surface area, refractory support is suitably selected from a variety of conventional refractory support materials such as silica, alumina, silica-alumina, diatomaceous earth, kieselguhr, spinel or titanium dioxide. Suitable refractory supports have surface areas in the range of about 10 to 600 $m^2/g$ and pore volumes of about 0.3 to 0.8 $cm^3/g$. In this regard refractory supports selected from silica and alumina are preferred with silica being most preferred. With the most preferred silica supports, it is desirable that the silica have a globular structure and that the pore volume be sufficient to accommodate the nickel halide e.g. nickel chloride crystallites, produced in the adsorption step without plugging off nickel containing sites on he solid adsorbent.

The solid adsorbents employed in the process of the invention may be prepared by any conventional process, for example, impregnation, co-precipitation or other metal deposition techniques, which allow for high metal loading and high diffusion into the porous support material selected. Suitably, multiple impregnations or metal depositions may be used to obtain the high metal loadings required for the solid absorbents of the present invention. As an alternative to preparation of the high metal loading solid supports, suitable metal e.g., nickel, loaded support materials are available from a variety of commercial suppliers including United Catalysts C-46 series nickel-on-silica or nickel-on-alumina materials. The solid absorbent is employed in particulate form in the process of the invention including any conventionally available particulate shape such as rings, spheres or spherical shaped particles, rods and the like. Prior to use in the process of the invention the solid absorbent is suitably treated with hydrogen or a reducing medium to insure that the metal is present in its metallic or metal hydride form.

The organic halide removal process of the invention may be conducted either batch-wise or continuously using techniques which are known in the art. Preferably, the process is carried out continuously using a fixed or fluidized bed technique, including optional recycle of treated hydrocarbon, with fixed bed processes being most preferred. In the fixed bed process, the hydrocarbon feedstock contaminated with minor amounts of organic halide, preferably organic chlorides, is percolated or passed through a column containing the solid metal and/or metal hydride adsorbent. In this regard since the metal and/or metal hydride may be somewhat soluble in liquid-phase aqueous based solvents, it is preferable that the hydrocarbon feedstock be anhydrous or substantially anhydrous—i.e. water contents of less than 0.1% by weight of the total feedstock being most preferred—if the solid absorbent contacting step is carried out under temperature and pressure conditions where the hydrocarbon feedstock is in the liquid phase. For vapor phase feedstreams, higher water contents can be tolerated provided the solid absorbent contacting step is carried out above the dew point of the feed. The volume of contaminated hydrocarbon feedstock which is treated by a given volume of solid adsorbent will vary, dependent on the concentration of organic halide contaminants present in the feedstock. However, for most feedstocks treated where the organic halide concentration is less than about 10,000 ppm, the volume of hydrocarbon feedstock to be used is from about 1 to 10,000 times the volume of the solid metal and/or metal hydride-containing adsorbent. The residence time of the hydrocarbon feed in contact with the absorbent typically ranges between from about 0.05 to 100 minutes with residence times in the range of about 5 to 60 minutes being preferred. Suitably the hydrocarbon feedstock is passed at a liquid hourly space velocity ("LHSV") of between about 0.01 to 100 with LHSV's in the range of about 0.1 to 10 being preferred. In the case of vapor phase feedstocks, the gas hourly space velocity is ("GHSV") typically in the range of about 100 to 10,000 hr-1. The operating temperatures for this adsorption step suitably range between 40 to 3000, preferably between about 100 and 210° C., and most preferably from about 140 to 190° C. The pressures employed in the absorption step are typically sufficient to maintain the hydrocarbon feedstock in a liquid state, with pressures in the range of 50 to 300 psig usually being sufficient; however, the operation of this adsorption step in the vapor or gaseous phase with consequent lower operating pressures is also within the scope of the process of the invention, for example, about 1 to 200 psig.

In the organic halide removal or adsorption step of the invention, the organic halide contaminants in the hydrocarbon feed are converted to insoluble metal halides on the refractory support. For example, in the most preferred aspect of the invention organic chloride contaminant in the hydrocarbon feedstock are converted into insoluble nickel chloride. At the point that substantially all of the accessible nickel or nickel hydride has been converted to $NiCl_2$ crystallites and/or the volume build up of $NiCl_2$ crystallites is such that any remaining untreated nickel or nickel hydride in the pores is effectively blocked from further reaction with organic halide, the adsorbent becomes saturated with organic chloride and the effluent from the column will gradually rise in chloride content until the effluent has the same chlorine content as the hydrocarbon feedstock. At this point the operation is stopped and the adsorbent is replaced with either fresh or regenerated adsorbent (see below) before the hydrocarbon feedstock is again passed through the adsorption column. Optionally and preferably, the adsorbent is regenerated in situ on a continuous basis. Since the metal and/or metal hydride containing adsorbent has some minor activity for side reactions such as polymerization of olefins, and the feed can contain heavy carbonaceous components, it is possible that some of the accessible metal or metal hydride in the solid adsorbent will be blocked from further reaction in the organic halide due to build up of carbonaceous residues, including polymeric materials. The regeneration process of the invention also functions to remove any carbonaceous residue or polymer which is formed. The other undesirable reactivity exhibited by the solid metal and/or metal hydride-containing absorbent at conditions necessary to effect removal of organic halides is the tendency to promote double bond isomerization where the hydrocarbon feed contains olefins or dienes. However, for typical feeds this reactivity under organic halide removal conditions is only minor, usually less than 20 percent of the olefinic bonds being subject to double bond migration, relative to the benefits achieved by removing the organic halide contaminants. In most cases, the process of the invention is capable of removing over 95 percent of the organic halides present in the hydrocarbon feedstream. In certain cases where it is desired to remove even higher amounts of the organic halide e.g., 99.9%+, it is possible to employ a staged operation where the hydrocarbon feed is contacted in one or more subsequent adsorbers containing the solid adsorbent after the initial adsorption stage where the bulk of the organic halide is removed.

In another aspect of the invention, the loaded solid adsorbent containing halide in the form of solid metal halide e.g. nickel chloride, from the organic halide removal step is regenerated by sequential treatment with (i) a reducing atmosphere to convert the metal halide to its metallic or reduced form, (ii) an oxidizing medium to remove any organic or carbonaceous deposits on the surface of the adsorbent thereby converting the metallic or reduced form of the metal to its oxide form, and (iii) a reducing atmosphere to convert the metal oxide to its reduced or metallic form thereby affording a regenerated solid adsorbent. The first step of this regeneration process may employ any conventional reducing medium such as hydrazine, hydrogen and the like and is preferably carried out by contacting the spent adsorbent with hydrogen gas at moderate partial pressures, for example, about 10 to 800 mm Hg, and moderate temperatures in the range of about 320 to 420° C. to convert the metal halide to its metallic and/or hydride form, with hydrogen halide gas being formed and removed as a gaseous effluent. In the second step of the regeneration process the treated adsorbent from the first step is treated with gaseous oxygen or an oxygen-containing gas at moderate partial pressures, about 10–800 mm Hg being suitable, and moderate temperatures in the range of about 320 to 420° C. to remove polymer and other organic deposits from the surface of the adsorbent, thereby converting the metal loaded on the adsorbent to its oxide form. The final step of the regeneration process is essentially a repeat of the first step wherein the metal oxide present on the solid adsorbent is converted to its metallic or metal hydride form with a hydrogen containing gas or other reductant at moderate partial pressures and temperatures as set forth above for the first step of the regeneration process. After regeneration the solid adsorbent is fully activated and ready for reuse in the organic halide removal step.

In some cases it has been found that the loaded solid adsorbent can be suitably regenerated by a two step process where the first step (step (i) in the paragraph immediately above) is eliminated and the loaded support is initially treated with an oxidizing medium as set forth above in step (ii) and then with a reducing atmosphere as set forth above in step (iii) with the contacting conditions being those which are described for steps (ii) and (iii) in the above paragraph. This optional two step regeneration process, wherein the initial treatment with a reducing medium is eliminated, forms another aspect of the present invention.

EXAMPLES

The following examples demonstrate some of the advantages achieved with the process of the invention in removing organic chloride contaminants from representative hydrocarbon streams.

General Procedures

All experiments shown in Examples 1–11 were carried out in liquid phase in a isothermal fixed bed reactor with a length/diameter ratio of more than 20. The pressure was maintained sufficient to keep feed in liquid phase (60–300 psig). Experiments shown in examples 12–13 were performed at 90 psig with the hydrocarbon stream in vapor phase.

Example 1

Liquid hydrocarbon feed, made up of isoctane and contaminated by 2000 mg/i-chlorobutane, was contacted with solid adsorbent containing 52% Ni on a silica support at a temperature of 170° C. and a liquid retention time 5 minutes. The absorbent which was obtained from United Catalysts (under the designation C46-7) had a surface area of 260 $m^2$/g, and a pore volume of 0.45 ml/g. The chlorine level in the reactor effluent was 3 mg/l giving a conversion of 99.8% of the organic chloride to insoluble nickel chloride which was retained on the support.

Example 2

Liquid isoctane feed contaminated with 2000 mg/l of 2-chloro 2-methylpropane, was contacted with the nickel on silica adsorbent of Example 1 at a temperature of 170° C. and a liquid retention time from 1 to 5 minutes. Chlorine level in the effluent was 1–3 mg/l for an organic chloride conversion of 99.8–99.9%.

Example 3

Liquid isoctane feed, contaminated by 2000 mg/l of chloroform, was contacted with the nickel on silica adsorbent of Example 1 at a temperature of 170° C. and a liquid retention time from 2.5 to 5 minutes. Chlorine level in the effluent was 1–3 mg/l at the first 4 hour of run and increased to 2000 ppm during the next hour.

Example 4

Liquid hydrocarbon feed, made up of isoctane contaminated by 2040 mg/l of 2-chloroethylbenzene, was contacted with the nickel on silica adsorbent of Example 1 at a temperature of 170° C. and a liquid retention time of 5 minutes.

Chlorine level in the effluent was 15 mg/l at the first 1 hour of run and increased to 1700 ppm during the next hour.

Example 5

Light raffinate, containing light hydrocarbons in the $C_5$–$C_7$ range (at least 20% of which are olefinic) and containing 600 mg/l of organic chlorides, was contacted with the nickel on silica adsorbent of Example 1 at a temperature of 170° C. and a liquid retention time of 5–20 minutes. Chlorine level in the effluent was maintained at 10 to 30 mg/l during a 16 hour run period.

Example 6

Light raffinate, containing light hydrocarbons in the $C_7$–$C_{10}$ range (at least 50% of which are olefinic) and contaminated by 1350 mg/l organic chlorine-containing compounds, was contacted with the nickel on silica adsorbent of Example 1 at a temperature of 170° C. and a liquid retention time of 5–20 minutes. Chlorine level in the effluent was maintained at 10 to 30 mg/l during a 16 hour run period.

Example 7

Light raffinate, containing light hydrocarbons in the $C_7$–$C_{10}$ range (at least 50% of which are olefinic) and contaminated by 1350 mg/i organic chlorine-containing compounds, was contacted with the nickel on silica adsorbent of Example 1 at a temperature of 170° C. and a liquid retention time of 10 minutes. Chlorine level in the effluent was maintained at 300–400 mg/l during a 36 hour run period.

Example 8

Light raffinate made up of $C_7$–$C_{10}$ hydrocarbons, at least 50% of which were olefinic, and contaminated by 1350 mg/l organic chlorine-containing compounds, was contacted with nickel on silica adsorbent of Example 1 at a temperature of 170° C. and liquid retention time of 5–20 minutes. Chlorine level in the effluent was maintained of 10 to 30 mg/l during a 16 hour run period.

Example 9

Light raffinate, containing $C_7$–$C_{10}$ hydrocarbons, at least 50% of which are olefinic, and contaminated by 1350 mg/l organic chlorine-containing compounds, was contacted with the nickel on silica adsorbent of Example 1 at a temperature of 170° C. and liquid retention time of 15 minutes, during a 12 hour run period. Conversion of organic chlorine to insoluble nickel chloride was more than 99%.

Upon completion of the 12 hour run period, the adsorbent was regenerated by flow of nitrogen with 10 mol % of hydrogen at 350° C. for 2 hours, then oxidized in a flow of nitrogen with low concentration of oxygen. The initial oxygen concentration in $N_2$ was about 0.3 volume %; the oxygen concentration was increased gradually to keep the temperature in the adsorbent bed not higher than 420° C. Finally, the absorbent was treated a second time with a diluted hydrogen stream 10 volume % at 420° C. for 2 hours.

Conversion of organic chlorine on regenerated absorbent during a 12 hour run period at 170° C. was 99%. A multi-cycle absorption-regeneration operation would employ the same conditions as the first cycle.

Example 10

A liquid hydrocarbon feed made up predominantly of methyl ethyl ketone and having the composition given in Table 1 below was passed through a fixed bed reactor (residence time of 20 minutes) containing a 58% Ni on $Al_2O_3$ adsorbent (available from United Catalysts under the designation C-46-8) at 155° C. and 90 psig. The initial chloride concentration of the feed was 460 ppmw and after 1 hour of run time the chloride content of the effluent was 2 ppmw.

TABLE 1

| Component | Concentration Percent by Weight |
| --- | --- |
| Ethanal | 0.0004 |
| Dichloromethane | 0.006 |
| Propanal | 0.05 |
| Propanone | 0.15 |
| Butanal | 0.37 |
| Methyl ethyl ketone | 98.7 |
| 2-Methyl-2-propanol | 0.005 |
| 2-Butanol | 0.18 |
| Methanoic Acid | 0.002 |
| 2-Pentanone | 0.30 |
| Mixed Butene Dimers | 0.005 |
| 2-Chloro-2-butanone | 0.04 |
| 1-Butanol | 0.07 |
| Ethanoic Acid | 0.004 |

TABLE 1-continued

| Component | Concentration Percent by Weight |
| --- | --- |
| 1-Chloro-2-propanone | 0.06 |
| 1,1-Dichlore-2-propanone | 0.007 |
| 1-Chloro-2-ethyl-2-propanol | 0.007 |
| 1-Chloro-2-butanone | 0.002 |

Example 11

Using the Ni on $Al_2O_3$ adsorbent of Example 10, a light hydrocarbon vapor phase stream containing a variety of olefinic and oxygenated components and having the composition given in Table 2 below was contacted at a temperature of 160° C. and pressure of 90 psig at 1000 hour-1 GHSV. The chlorine present in the vapor phase stream was removed at an efficiency of 99.8% during the first three hours of operation.

TABLE 2

| Component | Concentration Percent by Weight |
| --- | --- |
| Chloromethane | 0.03 |
| 2-Methylpropane | 50.7 |
| Butane | 30.3 |
| trans-2-Butene | 5.8 |
| cis-2-Butene | 3.4 |
| Ethanal | 2.7 |
| Dichloromethane | 0.007 |
| Propanal | 0.08 |
| Propanone | 0.09 |
| Butanal | 0.02 |
| 1-Chlorobutane | 0.07 |
| 2-Butanone | 5.0 |
| 2-Methyl-2-propanol | 0.0009 |
| 2-Butanol | 0.004 |
| Water | 0.84 |
| 2-Pentanone | 0.006 |
| 3-Chloro-2-butanone | 0.0009 |
| 1-Butanol | 0.0009 |
| 1-Chloro-2-propanone | 0.0009 |

Example 12

A vapor phase methyl ethyl ketone feed, with composition given in Table 1, was passed through a fixed bed containing the Ni/A1203 adsorbent of Example 10, at 151° C., 25 psig and a LHSV of 2.75 hour-1 (calculated as liquid flow to the reactor inlet). The observed chlorine removal efficiency was of 99.8%.

What is claimed:

1. A process for removing organic halide contaminants present in minor amounts in a hydrocarbon feedstock which comprises contacting the hydrocarbon feedstock with a solid adsorbent comprising a metal or metal hydride or mixture of metal and metal hydride wherein the metal is selected from nickel, cobalt and iron or mixtures thereof, on a porous, high surface area, refractory silica support with the metal and/or metal hydride comprising about 5 to 75 percent by weight of the solid adsorbent, whereby a least substantial portion of the organic halide present is converted to an insoluble halide salt of the supported metal or metal hydride, and thereby removed from the hydrocarbon feedstock, with the hydrocarbon feedstock being recovered after contact with the solid adsorbent substantially free of organic halide contaminants.

2. The process of claim 1 wherein the organic halide contaminants are selected from organic bromides, organic chlorides and mixtures thereof.

3. The process of claim 2 wherein the organic halide contaminants are organic chlorides.

4. The process of claim 1 wherein the metal making up the metal and metal hydride component of the solid adsorbent is nickel.

5. The process of claim 4 wherein the organic halide contaminants are organic chlorides.

6. The process of claim 1 wherein the solid adsorbent which is loaded with insoluble halide salt after contact with the hydrocarbon feedstock is regenerated by treatment with an oxidizing medium to remove any carbonaceous or organic deposits on the surface of the solid adsorbent followed by treatment with a reducing atmosphere to convert the metal halide on the solid adsorbent to its metallic or reduced form.

7. A process for removing organic halide contaminants present in minor amounts in a hydrocarbon feedstream which comprises:
   a) contacting the hydrocarbon feedstream with a solid adsorbent comprising a metal or metal hydride or mixture thereof wherein the metal is selected from nickel, cobalt and iron or mixtures thereof on a porous, high surface area, refractory support with the metal and/or metal hydride comprising about 5 to 75 percent by weight of the solid adsorbent, whereby substantially all of the halide present in the hydrocarbon feedstream reacts with the metal or metal hydride to form an insoluble metal halide thereby affording a hydrocarbon feedstream product substantially free of halide and a solid adsorbent loaded with metal halide;
   b) separating the metal halide loaded adsorbent from the hydrocarbon feedstream, substantially free of halide and contacting the separated adsorbent in sequential fashion with (i) a reducing atmosphere to convert the metal halide to its metallic or reduced form, (ii) an oxidizing medium to remove any carbonaceous or organic deposits on the surface of the adsorbent thereby converting the metallic or reduced form of the metal to its oxide form, and (iii) a reducing atmosphere to convert the metal oxide to its reduced or metallic form thereby affording a regenerated solid adsorbent;
   c) recycling the regenerated solid adsorbent back to step (a) of the process where it is used to remove additional halide from the hydrocarbon feedstream.

8. The process of claim 7 wherein the organic halide contaminants are selected from organic bromides, organic chlorides and mixtures thereof.

9. The process of claim 8 wherein the organic halide contaminants are organic chlorides.

10. The process of claim 7 wherein the metal making up the metal or metal hydride component of the solid adsorbent is nickel.

11. The process of claim 10 wherein the organic halide contaminants are organic chlorides.

12. The process of claim 7 or 11 wherein the refractory support is silica or alumina.

13. The process of claim 7 or 11 wherein the refractory support is silica.

* * * * *